(12) United States Patent
Thorsby et al.

(10) Patent No.: US 8,507,015 B2
(45) Date of Patent: Aug. 13, 2013

(54) COMPOSITION FOR COUNTERING THE EFFECTS OF ALCOHOL CONSUMPTION

(75) Inventors: Cason Thorsby, Mt. Pleasant, MI (US); Curtis Thorsby, Mt. Pleasant, MI (US)

(73) Assignee: Lquid Innovations, LLC, Bay City, MI (US)

( * ) Notice: Subject to any disclaimer, the term of this patent is extended or adjusted under 35 U.S.C. 154(b) by 7 days.

(21) Appl. No.: 13/037,717

(22) Filed: Mar. 1, 2011

(65) Prior Publication Data

US 2011/0217392 A1 Sep. 8, 2011

Related U.S. Application Data

(60) Provisional application No. 61/351,627, filed on Jun. 4, 2010, provisional application No. 61/309,975, filed on Mar. 3, 2010.

(51) Int. Cl.
*A61K 36/82* (2006.01)
*A61K 36/33* (2006.01)
*A61K 36/00* (2006.01)

(52) U.S. Cl.
USPC .......................... 424/729; 424/767; 424/778

(58) Field of Classification Search
None
See application file for complete search history.

(56) References Cited

U.S. PATENT DOCUMENTS

| | | |
|---|---|---|
| 4,006,219 A | 2/1977 | Upham et al. |
| 4,496,548 A | 1/1985 | Moldowan et al. |
| 4,808,574 A | 2/1989 | Breckhman et al. |
| 5,009,891 A | 4/1991 | Niwa |
| 5,547,671 A | 8/1996 | Duthinh |
| 5,958,933 A | 9/1999 | Naftchi |
| 6,077,838 A | 6/2000 | Hausheer |
| 6,913,769 B2 | 7/2005 | Oslick et al. |
| 6,967,031 B1 | 11/2005 | Oslick et al. |
| 7,063,865 B2 * | 6/2006 | Jones et al. .................. 424/646 |
| 2002/0192303 A1 | 12/2002 | Arver et al. |
| 2005/0271739 A1 * | 12/2005 | Wang ........................... 424/562 |
| 2006/0222682 A1 | 10/2006 | Andrews |
| 2008/0279786 A1 | 11/2008 | Cash |
| 2009/0004326 A1 | 1/2009 | Andrews |
| 2010/0316735 A1 * | 12/2010 | Belliston ..................... 424/682 |

* cited by examiner

*Primary Examiner* — Chris R Tate
*Assistant Examiner* — Deborah Davis
(74) *Attorney, Agent, or Firm* — Technology Law PLLC; Karen L. Kimble

(57) ABSTRACT

This invention provides a composition and method for countering the effects of alcohol consumption by a person. The composition provided is a specifically proportion combination of various vitamins, potassium, magnesium, milk thistle extract, amino acids, green tea extract, prickly pear extract, malic acid, and optionally Maqui berry extract, and various other additives for flavor and preservatives for a liquid formulation. The method includes orally administering the composition to a person under the influence of alcohol.

6 Claims, No Drawings

COMPOSITION FOR COUNTERING THE EFFECTS OF ALCOHOL CONSUMPTION

CROSS REFERENCE TO RELATED APPLICATIONS

This application claims priority and benefit from U.S. Provisional Patent Application 61/351,627, filed on Jun. 4, 2010 and U.S. Provisional Patent Application 61/309,975, filed on Mar. 3, 2010.

BACKGROUND OF THE INVENTION

To varying degrees persons frequently over consume alcohol or are highly susceptible to its effects. The two most common such effects are intoxication and a "hang-over". These effects may vary from mild or hardly noticeable to severe in any person. Having persons who are under the influence of alcohol try to drive a vehicle on the public roads has posed serious problems for that person as well as any non-drinker they may encounter; many deaths every year are attributed to such impaired drivers. Thus this poses a serious public safety concern.

Some prior efforts to sober such a person up quickly have involved having them drink coffee. Unfortunately, all the coffee does is make a wide-awake drunk.

Have such a drunk "sleep it off" is effective, which is the main reason they are arrested or retained until the next morning or to provide a sufficient time lapse for the body to have reduced the effects of the alcohol and thereby "sober up". Alcohol is a carbohydrate and is metabolized though various body metabolism cycles in the liver to form carbon dioxide and water and thereby is removed from the blood and tissues, whereupon the drunk becomes sober.

To remove or lesson the hang-over effects in a person any myriad of remedies and products have been used such as food combinations, beverages, medicines, and breathing oxygen deeply.

U.S. Pat. No. 4,006,219 discloses a specific composition for treatment of hang-over. This composition must be protected against overexposure to heat, light, moisture and oxygen. It is preferably in a sealed tablet form.

U.S. Pat. No. 6,913,769 describes the composition and U.S. Pat. No. 6,967,031 describes the method of using it, where a composition has silymarin and silbin as the active components but also requires manganese and molybdenum and has no other natural additives as active components.

Clearly, it would be desirable to have a readily available, inexpensive and easy to use product that will counter the effects of such alcohol consumption quickly to reduce or prevent a hang-over.

BRIEF SUMMARY OF THE INVENTION

The present invention provides a composition and method for countering the effects of alcohol consumption. Thus, in one aspect of the present invention an aqueous composition for reducing the intoxicating effects associated with the consumption of alcoholic beverage by humans, which composition consists essentially of: vitamins, potassium, magnesium, malic acid, milk thistle extract, amino acids, green tea extract, prickly pear extract, and various other additives for flavor and preservatives with DI water for an aqueous composition is described. Such aqueous compositions can take many forms, for example, a dose as a liquid in a vial that can be completely consumed such as in a 2 oz pre-packaged form; a fifth bottle where the dose is measured out with a shot glass or pump and then consumed; a dose pre-added to a liquid beverage such as syrups, slushies; smoothies; and others. Other forms for administering the composition of this invention are as powders that have the dose stirred or added into the liquid just before or in the preparation of the food or ingested item for consumption such as tea bags, beverages, and others; or the dose is added to the food or ingested item and consumed such as a sorbet or slushies or smoothies and others. Also the dose can be pre-added to solid forms of stick packs; gum; gummies; hard candy; tablets including but not limited to those that are chewed or dissolved in water or dissolve in the mouth; capsules; gels; popsicles, fruit roll-ups; and others that can have the dose coated on the solid form or mixed into the food prior to its final formation and then comes in contact with water in the body.

More specifically, a composition containing a combination of ingredients in specific proportions is provided, which when administered to a person soon after completion of consumption of alcoholic beverages, especially soon after the last beverage, can reduce or eliminate the effects of intoxication and hang-over quickly and effectively or even prevent them from occurring. This invention provides a method for reducing the intoxicating effects associated with the consumption of alcoholic beverages by a person, which method comprises orally administering to said intoxicated person a composition consisting essentially of: the composition described herein, in a single 2 oz dose in any of these forms, administered after ceasing consumption of alcoholic beverages. Unexpectedly, usually only 1 dose is required regardless of age, weight, gender or amount of alcoholic beverages consumed. The dose is preferably an aqueous liquid, such as a 2 oz shot of the present composition; but alternatively the dose may be a powder that is coated onto a food or ingestible item or mixed into the food as described herein.

This composition is detailed below is one example and is administered as a single liquid dosage form having various natural ingredients. The method comprises orally administering an effective amount of the composition to a person, preferably shortly after cessation of consumption of alcoholic beverages.

DETAILED DESCRIPTION OF THE INVENTION

It is understood that the terminology used herein is for the purpose of describing particular embodiments only and is not intended to be limiting. As used in this specification, the singular forms "a", "an", and "the" include plural referents unless the content clearly indicates otherwise.

Also, certain US patents have been incorporated by reference. However, the text of such patents is only incorporated by reference to the extent that no conflict exists between such text and other statements and drawings set forth herein. In the event of such conflict, then any such conflicting text in such incorporated by reference US patent is specifically not so incorporated in this patent.

GLOSSARY

The following terms as used in this application are to be defined as stated below and for these terms, the singular includes the plural. All these components are readily available commercially from suppliers such as Nutricaps Labs, Inc., Vitacap Labs, Vitakem Labs, Allen Flavors, Inc. and others.

L-Alanine is a non-essential amino acid and is readily available either as a natural or synthetic product, and as a powder Alcohol means ethyl alcohol Alcoholic beverage means any popular spirits or blends containing ethyl alcohol and intended for human consumption Aqueous composition means a dose of the present composition in an aqueous form in any food or ingestible item that can be consumed or a dose in a powder form that can be pre-mixed into a liquid, ingested item or food and consumed in an aqueous form or that later becomes aqueous upon ingestion DI water means water acceptable for human consumption that has also been filtered several times and meets the government guidelines for water for this use, including deionized water that may be further filtered L-Glutamine is a non-essential amino acid and is readily available either as a natural or synthetic product, and as a powder L-Glutathione means an amino acid compound of glutamic acid, cysteine and glycine, $C_{10}H_{17}H_6N_3S$, which can separate into these amino acids by hydrolysis Green tea extract has as its most important ingredients catechins, theanine and caffeine Hang-over is a relative term and not amenable to precise measurement or description Pantothenic acid is a part of the vitamin B complex and a component of coenzyme A, is readily available from a number of sources, either as a natural or synthetic product, and is generally a viscous liquid Potassium citrate, $K_3C_6H_5O_7.H_2O$, is often used with vitamins as a stabilizer and buffer Prickly pear extract is from cactus *Opuntia ficus-indica*

Magnesium lactate, also magnesium 2-hydroxypropanoate, $C_6H_{10}MgO_6$

Malic acid, $CO_2HCH_2CH(OH)CO_2H$, is also known as apple acid

Maqui berry extract is from *Aristotelia chilensis* (Maqui or Chilean Wineberry) a species of the Elaeocarpaceae family native to the Valdivian temperate rainforests of Chile and adjacent regions of southern Argentina, and is available from various sources, has high levels of antioxidants, and is considered a super fruit and helps the body detoxify Milk thistle extract is from the seeds of the genus *Silybum* Adans, which is known for liver protection Vitamin A, as its acetate, is readily available from a number of sources, either as a natural or synthetic product, and is generally in a powdered form or liquid, and can be carotene Vitamin C is readily available from a number of sources, either as a natural or synthetic product, and is generally in a powdered form or liquid and can be ascorbic acid Vitamin E, as its acetate, is readily available from a number of sources, either as a natural or synthetic product, and is generally in a liquid (viscous oil) form and can be tocopherol Vitamin B1 is readily available from a number of sources, either as a natural or synthetic product, and is generally in a powdered form or liquid and can be thiamine as the hydrochloride or mononitrate salt Vitamin B2 is readily available from a number of sources, either as a natural or synthetic product, and is generally in a powdered form or liquid and can be riboflavin Vitamin B6 is readily available from a number of sources, either as a natural or synthetic product, and is generally in a powdered form or liquid Vitamin B5 is readily available from a number of sources, either as a natural or synthetic product, and is generally in a powdered form or liquid and can be dicalcium pantothenate Vitamin B12 is readily available from a number of sources, either as a natural or synthetic product, and is generally in a powdered form or liquid and can be cyanocobalamin.

The composition of this invention has various combinations of components. The comparative simplest composition is milk thistle extract and water (Composition 1). To improve on its effectiveness, vitamin B complex, vitamin C, potassium, and magnesium were added to Composition 1 (Composition 2, also comparative). A further composition (Composition 3) was made that is a composition of this invention (as detailed in Example 4) where vitamin A, vitamin E, malic acid, prickly pear extract, green tea extract, L-glutamine, and L-alanine were added to Composition 2. Another composition of this invention was made where glutathione (or its component amino acids) was added to Composition 3 (as detailed in Example 5). Still another composition of this invention was made where the composition in Example 5 has the vitamin B12 decreased, Maqui berry extract added, and the amount of L-glutamine and L-alanine modified.

The amino acids used in the present composition are L-glutamine and L-alanine and optionally L-glutathione or its component amino acids of glutamic acid, cysteine and glycine.

The vitamins used in the present composition are A, C, E, B1, B2, B6, B12 and B5.

Various additives are added to Composition 3 or 4 or 5 for color, flavor or preservative of the final aqueous composition, such additives include sodium benzoate, potassium sorbate, malic acid, calcium disodium EDTA, sucralose, flavors (such as natural flavors or artificial as used in beverages and foods) and DI water. Some of the flavors possible are wild berry pomegranate, orange, fruit punch, acai berry, and lemon lime as well as others. DI Water is present in 92-95% by wt of the final aqueous dose. The final composition is an aqueous solution. When a powder is desired, the aqueous solution is freeze-dried or evaporated to form the powder in the desired dose.

Of the added ingredients in Composition 3 or 4 or 5, malic acid is used to reduce the poisonous effects of alcohol in the body and boost immunity. It also enhances the overall flavor. There is no sugar (sucrose or calorie sweetener) added. Sucralose is used as a zero calorie sweetener but other acceptable sweeteners are stevia, Lo Han, acesulfame potassium, arthenol, xylitol, and inotyol. Potassium sorbate is a preservative and inhibits mold and yeast. Sodium benzoate is a preservative and inhibits bacteria. Calcium disodium EDTA prevents vitamin C from reacting with sodium benzoate. The amount of DI water present is enough to get the desired solution and dose of the actives.

The composition effectively reduces or prevents the physical and mental side effects caused by consuming alcohol. The usual dose is 2 ounces, usually sold as a shot of the composition of this invention. Only one dose of 2 ounces is needed to obtain the desired effect. It is also contemplated that the composition of this invention may be sold as a fifth (25.6 oz) to a bar where it can then be divided into the individual doses and sold as the last shot for a person in the bar. The other aqueous compositions that are possible have been discussed above.

The dose of the composition of this invention should be taken soon after the last alcoholic drink is consumed. While not wishing to be bound by theory, it is believed that this composition helps replenish the body of the person who drinks by replacing those components it looses while consuming alcohol. Only one 2 ounce dose is required, taken shortly after the person's consumption of alcohol ceases in order to have some or all of the desired effects of: waking up feeling up-beat, energetic and/or better than if they had not drank at all or without any sluggishness or headache, and able do their normal activities the next morning without any appreciable difficulty.

The invention will be further clarified by a consideration of the following examples, which are intended to be purely exemplary of the present invention.

EXAMPLES

Example 1

Milk Thistle Extract Composition (Comparative)

An initial composition used a single active ingredient of milk thistle. The persons (about 50) who used this composition noticed how their body felt rejuvenated rather than as fatigued, but still had a headache and tired.

Example 2

Milk Thistle Extract, Vitamin B Complex, Vitamin C, Potassium and Magnesium Composition (Comparative)

The persons (about 50) who took this composition were surprised at how well they felt after a night of drinking; however, they were still tired and some had a headache.

Example 3

Milk Thistle Extract, Prickly Pear Extract, Green Tea Extract, L-Glutamine, L-Alanine, Malic Acid, Vitamin B Complex, Vitamin C, Vitamin E, Vitamin A, Potassium and Magnesium Composition The persons (about 50) who took this composition (as defined in Example 4) were claiming that they woke up feeling up-beat, energetic and better than they would have if they had not drank at all without any sluggishness. They did not have any headache but were slightly dehydrated. They could do their normal activities the next morning without any difficulty. Only one 2 ounce dose of this composition was required to attain this effect regardless of the person's age, gender, weight or amount of alcoholic beverage consumed. The preferred dose is taken shortly after alcohol beverage drinking has ceased.

Example 4

Preparation of Composition 3

| Product: Party Armor ™ Serving Size: 2 oz. (16 mL), Servings Per Container: 1 | | |
|---|---|---|
| Ingredient | Amount Per Serving | % Daily Value† |
| Calories | 0 | |
| Total Fat | 0 g | 0%* |
| Total carbohydrates | 0 g | 0%* |
| Dietary Fiber | 0 g | 0%* |
| Sugar | 0 g | |
| Protein | 0 g | 0%* |

†Percent Daily Value is based on a 2,000 calorie diet.
*Daily Value not established.

The components are listed in the table below.
Amount of components per 2 oz dose:

| Ingredient | Amount | % Daily Value† |
|---|---|---|
| Vitamin A (as Retinyl Palmitate) | 100-500 IU | 10 |
| Vitamin C (as Ascorbic Acid) | 50-350 mg | 583 |
| Vitamin E (as dl-alpha Tocopheryl Acetate) | 2-4 IU | 10 |
| Vitamin B1 (as Thiamin HCl) | 0.5-1.5 mg | 80 |
| Vitamin B2 (as Riboflavin) | 1-2 mg | 100 |
| Vitamin B5 (as D-Calcium Pantothenate) | 5-30 mg | 300 |
| Vitamin B6 (as Pyridoxine HCl) | 1-3 mg | 100 |
| Vitamin B12 (as Cyanocobalamin) | 2 mcg-1 mg | 16667 |
| Potassium (as Potassium Citrate) | 50-100 mg | 2 |
| Magnesium (as Magnesium lactate) | 10-25 mg | 6 |
| Malic Acid | 10-600 mg | † |
| Milk Thistle Extract | 25-200 mg | † |
| L-Glutamine | 50-100 mg | † |
| L-Alanine | 50-100 mg | † |
| Green Tea Extract | 50-100 mg | † |
| Prickly Pear Extract | 40-100 mg | † |
| OTHER INGREDIENTS | | |
| Sodium Benzoate | * | |
| Potassium Sorbate | * | |
| Flavor-natural | * | |
| Calcium Disodium EDTA | * | |
| Sucralose | * | |
| DI Water | 92-95% by wt | |

†Percent Daily Values are based on a 2,000 calorie diet.
*The Other Ingredients are present in minor amounts.

To the DI water in a batch tank was added the sodium benzoate and potassium sorbate with stirring until dissolved. The vitamins were added as a commercially available premix and the amino acids and other natural ingredients with stiffing for about 5-20 minutes. The desired flavoring and malic acid were added with further stirring for about 5-20 minutes. More DI water was then added to have a final pH of about 3.5 to about 4.5. The aqueous solution was then divided into the 2 oz size and packaged.

Example 5

Preparation of Composition 4

| Product: Party Armor ™ Serving Size: 2 oz. (16 mL), Servings Per Container: 1 | | |
|---|---|---|
| Ingredient | Amount Per Serving | % Daily Value† |
| Calories | 0 | |
| Total Fat | 0 g | 0%* |

-continued

Product: Party Armor ™
Serving Size: 2 oz. (16 mL), Servings Per Container: 1

| Ingredient | Amount Per Serving | % Daily Value† |
|---|---|---|
| Total carbohydrates | 0 g | 0%* |
| Dietary Fiber | 0 g | 0%* |
| Sugar | 0 g | |
| Protein | 0 g | 0%* |

†Percent Daily Value is based on a 2,000 calorie diet.
*Daily Value not established.

The components are listed in the table below.
Amount of components per 2 oz dose:

| Ingredient | Amount | | % Daily Value† |
|---|---|---|---|
| Vitamin A (as Retinyl Palmitate) | 100-500 | IU | 10 |
| Vitamin C (as Ascorbic Acid) | 50-350 | mg | 583 |
| Vitamin E (as dl-alpha Tocopheryl Acetate) | 2-4 | IU | 10 |
| Vitamin B1 (as Thiamin HCl) | 0.5-1.5 | mg | 80 |
| Vitamin B2 (as Riboflavin) | 1-2 | mg | 100 |
| Vitamin B5 (as D-Calcium Pantothenate) | 5-30 | mg | 300 |
| Vitamin B6 (as Pyridoxine HCl) | 1-3 | mg | 100 |
| Vitamin B12 (as Cyanocobalamin) | 2 mcg-1 | mg | 16667 |
| Potassium (as Potassium Citrate) | 50-100 | mg | 2 |
| Magnesium (as Magnesium lactate) | 10-25 | mg | 6 |
| Malic Acid | 10-600 | mg | † |
| Milk Thistle Extract | 20-200 | mg | † |
| L-Glutamine | 50-100 | mg | † |
| L-Glutathione | 20-100 | mg | † |
| L-Alanine | 50-100 | mg | † |
| Green Tea Extract | 50-100 | mg | † |
| Prickly Pear Extract | 40-100 | mg | † |
| OTHER INGREDIENTS | | | |
| Sodium Benzoate | | | * |
| Potassium Sorbate | | | * |
| Flavor-natural | | | * |
| Calcium Disodium EDTA | | | * |
| Sucralose | | | * |
| DI Water | 92-95% by wt | | |

†Percent Daily Values are based on a 2,000 calorie diet.
*The Other Ingredients are present in minor amounts.

To the DI water in a batch tank was added the sodium benzoate and potassium sorbate with stirring until dissolved. The vitamins were added as a commercially available premix and the amino acids and other natural ingredients with stirring for about 5-20 minutes. The desired flavoring and malic acid were added with further stirring for about 5-20 minutes. More DI water was then added to have a final pH of about 3.5 to about 4.5. The aqueous solution was then divided into the 2 oz size and packaged.

Example 6

Preparation of Composition 5

Product: Party Armor ™
Serving Size: 2 oz. (16 mL), Servings Per Container: 1

| Ingredient | Amount Per Serving | % Daily Value† |
|---|---|---|
| Calories | 0 | |
| Total Fat | 0 g | 0%* |
| Total carbohydrates | 0 g | 0%* |
| Dietary Fiber | 0 g | 0%* |
| Sugar | 0 g | |
| Protein | 0 g | 0%* |

†Percent Daily Value is based on a 2,000 calorie diet.
*Daily Value not established.

The components are listed in the table below.
Amount of components per 2 oz dose:

| Ingredient | Amount | | % Daily Value† |
|---|---|---|---|
| Vitamin A (as Retinyl Palmitate) | 100-500 | IU | 10 |
| Vitamin C (as Ascorbic Acid) | 50-350 | mg | 583 |
| Vitamin E (as dl-alpha Tocopheryl Acetate) | 2-4 | IU | 10 |
| Vitamin B1 (as Thiamin HCl) | 0.5-1.5 | mg | 80 |
| Vitamin B2 (as Riboflavin) | 1-2 | mg | 100 |
| Vitamin B5 (as D-Calcium Pantothenate) | 5-30 | mg | 300 |
| Vitamin B6 (as Pyridoxine HCl) | 1-3 | mg | 100 |
| Vitamin B12 (as Cyanocobalamin) | 2-500 | mcg | 8333 |
| Potassium (as Potassium Citrate) | 50-100 | mg | 2 |
| Magnesium (as Magnesium lactate) | 10-25 | mg | 6 |
| Malic Acid | 10-600 | mg | † |
| Milk Thistle Extract | 20-200 | mg | † |
| L-Glutamine | 50-300 | mg | † |
| L-Glutathione | 20-100 | mg | † |
| L-Alanine | 50-300 | mg | † |
| Green Tea Extract | 50-100 | mg | † |
| Prickly Pear Extract | 40-100 | mg | † |
| Maqui Berry Extract | 10-500 | mg | † |
| OTHER INGREDIENTS | | | |
| Sodium Benzoate | | | * |
| Potassium Sorbate | | | * |
| Flavor-natural | | | * |
| Calcium Disodium EDTA | | | * |
| Sucralose | | | * |
| DI Water | 92-95% by wt | | |

†Percent Daily Values are based on a 2,000 calorie diet.
*The Other Ingredients are present in minor amounts.

To the DI water in a batch tank was added the sodium benzoate and potassium sorbate with stirring until dissolved. The vitamins were added as a commercially available premix and the amino acids and other natural ingredients with stirring for about 5-20 minutes. The desired flavoring and malic acid were added with further stirring for about 5-20 minutes. More DI water was then added to have a final pH of about 3.5 to about 4.5. The aqueous solution was then divided into the 2 oz size and packaged.

These examples are the preferred embodiments but are not limiting for the specific components that are not the active components. The composition has been tested, but it is not to be assumed that this composition will always be effective for every person, but it has proven to be very effective in the persons tested.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter. Accordingly, this description is to be construed as illustrative only and is for the purpose of teaching those skilled in the art the general manner of carrying out the invention.

What is claimed is:

1. An aqueous composition for reducing the intoxicating effects associated with the consumption of alcoholic beverages by humans, wherein the composition comprises: 100-500 IU of vitamin A; 50-350 mg of vitamin C; 2-4 IU of vitamin E; 0.5-1.5 mg of vitamin B1; 1-2 mg vitamin B2; 5-30 mg of vitamin B5; 1-3 mg of vitamin B6; 2-500 mcg of vitamin B12; 50-100 mg of potassium citrate; 10-25 mg of magnesium lactate; 20-200 mg of milk thistle extract; 10-600 mg of malic acid; 50-300 mg of each of L-glutamine and L-alanine; 50-100 mg of green tea extract; 40-100 mg of prickly pear extract; 10-500 mg of Maqui berry extract; and ingredients for color, flavor, and stability, with 92-95% wt. of DI water.

2. The composition of claim 1 wherein the additional amino acid L-glutathione or its component amino acids consisting of glutamic acid, cysteine and glycine are present.

3. The composition of claim 2 wherein 20-100 mg of L-glutathione is added.

4. The composition of claim 1, wherein the composition additionally contains one or more of preservatives of sodium benzoate, potassium sorbate, or calcium disodium EDTA, sweetener of sucralose, and flavoring.

5. The composition of claim 1, wherein the flavor ingredient is wild berry pomegranate, orange, fruit punch, acai berry or lemon lime.

6. The composition of claim 1 wherein the aqueous composition is freeze-dried or evaporated to form a powder.

* * * * *